(12) United States Patent
Allen et al.

(10) Patent No.: US 10,736,600 B2
(45) Date of Patent: Aug. 11, 2020

(54) X-RAY IMAGING DETECTOR WITH INDEPENDENTLY SLEEPABLE PROCESSORS

(71) Applicant: VAREX IMAGING CORPORATION, Salt Lake City, UT (US)

(72) Inventors: Maxwell Allen, Redwood City, CA (US); William Hornof, Carlsbad, CA (US); Martin Klausmeier-Brown, Indianapolis, IN (US); Cameron Love, Carlsbad, CA (US)

(73) Assignee: VAREX IMAGING CORPORATION, Salt Lake City, UT (US)

( * ) Notice: Subject to any disclaimer, the term of this patent is extended or adjusted under 35 U.S.C. 154(b) by 37 days.

(21) Appl. No.: 15/867,716

(22) Filed: Jan. 11, 2018

(65) Prior Publication Data
US 2018/0368801 A1  Dec. 27, 2018

Related U.S. Application Data

(60) Provisional application No. 62/587,433, filed on Nov. 16, 2017, provisional application No. 62/522,721, filed on Jun. 21, 2017.

(51) Int. Cl.
*A61B 6/00* (2006.01)
*G16H 40/63* (2018.01)
(Continued)

(52) U.S. Cl.
CPC ............ *A61B 6/563* (2013.01); *A61B 6/4283* (2013.01); *A61B 6/4405* (2013.01); *A61B 6/461* (2013.01);
(Continued)

(58) Field of Classification Search
CPC ....... A61B 6/563; A61B 6/461; A61B 6/4283; A61B 6/566; A61B 6/56; A61B 6/5294;
(Continued)

(56) References Cited

U.S. PATENT DOCUMENTS

| | | | |
|---|---|---|---|
| 2004/0146142 A1* | 7/2004 | Maijala | A61B 6/4405 378/102 |
| 2006/0054833 A1 | 3/2006 | Tsuchino et al. | |

(Continued)

FOREIGN PATENT DOCUMENTS

| | | |
|---|---|---|
| JP | 2007330274 A | 12/2007 |
| JP | 2010051523 A | 3/2010 |

(Continued)

OTHER PUBLICATIONS

DICOM standard [online]. [retrieved on Oct. 9, 2019]. Retrieved from the internet:<https://www.dicomstandard.org/>. (Year: 2019).*

(Continued)

*Primary Examiner* — Christine S. Kim
(74) *Attorney, Agent, or Firm* — SU IP Consulting

(57) ABSTRACT

An X-ray imaging detector comprises at least one wireless transceiver configured to download study data from at least one external server, a digital image sensor configured to generate a plurality of signals in response to x-rays incident on the imaging detector, and at least one processor communicatively coupled to the imaging detector and the radio. The at least one processor is configured to receive the plurality of signals and generate a digital representation of an x-ray image based on the plurality of signals and associate the digital representation to the study data.

25 Claims, 6 Drawing Sheets

(51) Int. Cl.
*G06F 16/58* (2019.01)
*G16H 30/20* (2018.01)
*G16H 80/00* (2018.01)
*G06T 5/00* (2006.01)
*H04L 29/08* (2006.01)

(52) U.S. Cl.
CPC ............ *A61B 6/462* (2013.01); *A61B 6/5294* (2013.01); *A61B 6/56* (2013.01); *A61B 6/566* (2013.01); *G06F 16/5866* (2019.01); *G06T 5/009* (2013.01); *G16H 30/20* (2018.01); *G16H 40/63* (2018.01); *G16H 80/00* (2018.01); *A61B 2560/0214* (2013.01); *G06T 2200/24* (2013.01); *G06T 2207/10116* (2013.01); *G06T 2207/20208* (2013.01); *H04L 67/02* (2013.01)

(58) Field of Classification Search
CPC .................. A61B 6/462; A61B 6/4405; A61B 2560/0214; G06F 16/5866; G16H 30/20; G16H 80/00; G16H 40/63; G06T 5/009; G06T 2200/24; G06T 2207/10116; G06T 2207/20208; H04L 67/02
See application file for complete search history.

(56) References Cited

U.S. PATENT DOCUMENTS

| | | | | |
|---|---|---|---|---|
| 2006/0100979 A1* | 5/2006 | Venturino | ........... | G06F 3/03543 |
| 2006/0261296 A1* | 11/2006 | Heath | ..................... | G03B 42/02 |
| | | | | 250/580 |
| 2010/0049740 A1* | 2/2010 | Iwase | ..................... | G06F 19/321 |
| | | | | 705/7.27 |
| 2010/0054417 A1 | 3/2010 | Nishino et al. | | |
| 2011/0110496 A1* | 5/2011 | Foos | ..................... | A61B 6/4405 |
| | | | | 378/98.5 |
| 2012/0189098 A1* | 7/2012 | Liu | ..................... | A61B 6/4283 |
| | | | | 378/62 |
| 2012/0189099 A1* | 7/2012 | Liu | ..................... | A61B 6/4233 |
| | | | | 378/62 |
| 2013/0202085 A1* | 8/2013 | Petrick | ..................... | H04N 5/32 |
| | | | | 378/62 |
| 2014/0064454 A1 | 3/2014 | Hammond et al. | | |
| 2014/0254758 A1 | 9/2014 | Saigusa | | |
| 2014/0254760 A1 | 9/2014 | Hiroike et al. | | |
| 2014/0362975 A1 | 12/2014 | Garcia et al. | | |
| 2015/0216497 A1* | 8/2015 | Hayashi | ................. | A61B 6/566 |
| | | | | 378/62 |
| 2015/0223767 A1 | 8/2015 | Sehner et al. | | |
| 2016/0335985 A1* | 11/2016 | Ebberson | ................. | G09G 5/02 |
| 2017/0311920 A1* | 11/2017 | Hiroshige | ................ | A61B 6/00 |

FOREIGN PATENT DOCUMENTS

| | | |
|---|---|---|
| JP | 2014171520 A | 9/2014 |
| JP | 2014171522 A | 9/2014 |
| JP | 2015532143 A | 11/2015 |
| WO | 2016084517 A1 | 6/2016 |
| WO | 2017005482 A1 | 1/2017 |

OTHER PUBLICATIONS

The Extended European Search Report, Application No. 18178046.1, Nov. 12, 2018.

* cited by examiner

X-RAY IMAGING DETECTOR WITH INDEPENDENTLY SLEEPABLE PROCESSORS

CROSS-REFERENCE TO RELATED APPLICATIONS

The present application claims the benefit of the U.S. Provisional Application No. 62/522,721, filed Jun. 21, 2017, and the U.S. Provisional Application 62/587,433, filed Nov. 16, 2017. These United States Provisional applications, including any appendices or attachments thereof, are incorporated herein by reference in their entirety.

BACKGROUND

Unless otherwise indicated herein, the approaches described in this section are not prior art to the claims in this application and are not admitted to be prior art by inclusion in this section.

Digital radiography is a form of X-ray imaging in which digital X-ray imaging detectors are used to generate digital X-ray images, and has multiple advantages over traditional film-based techniques. By bypassing chemical processing, digital radiography is more time efficient, provides digital images for immediate image preview, facilitates image enhancement, and generally requires less radiation to produce an image of similar contrast.

Digital radiography is now used in many applications, including medical diagnostics, veterinary care, dental imaging, industrial inspection, and security. Each of these applications could benefit from a completely portable implementation of an X-ray acquisition system, i.e., battery-powered device with full image acquisition, enhancement, and data storage capabilities. However, the power requirements of conventional digital X-ray devices preclude such a completely portable device. For example, while X-ray imaging detectors have been developed with a form factor that can be easily carried, the size and power requirements of the associated image acquisition work station generally prevents such a system from being implemented as a single self-contained, battery powered device. Instead, in conjunction with an X-ray imaging detector, a dedicated computer workstation is typically employed for receiving acquired images, performing image processing and enhancement, and providing a user interface for controlling image acquisition.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
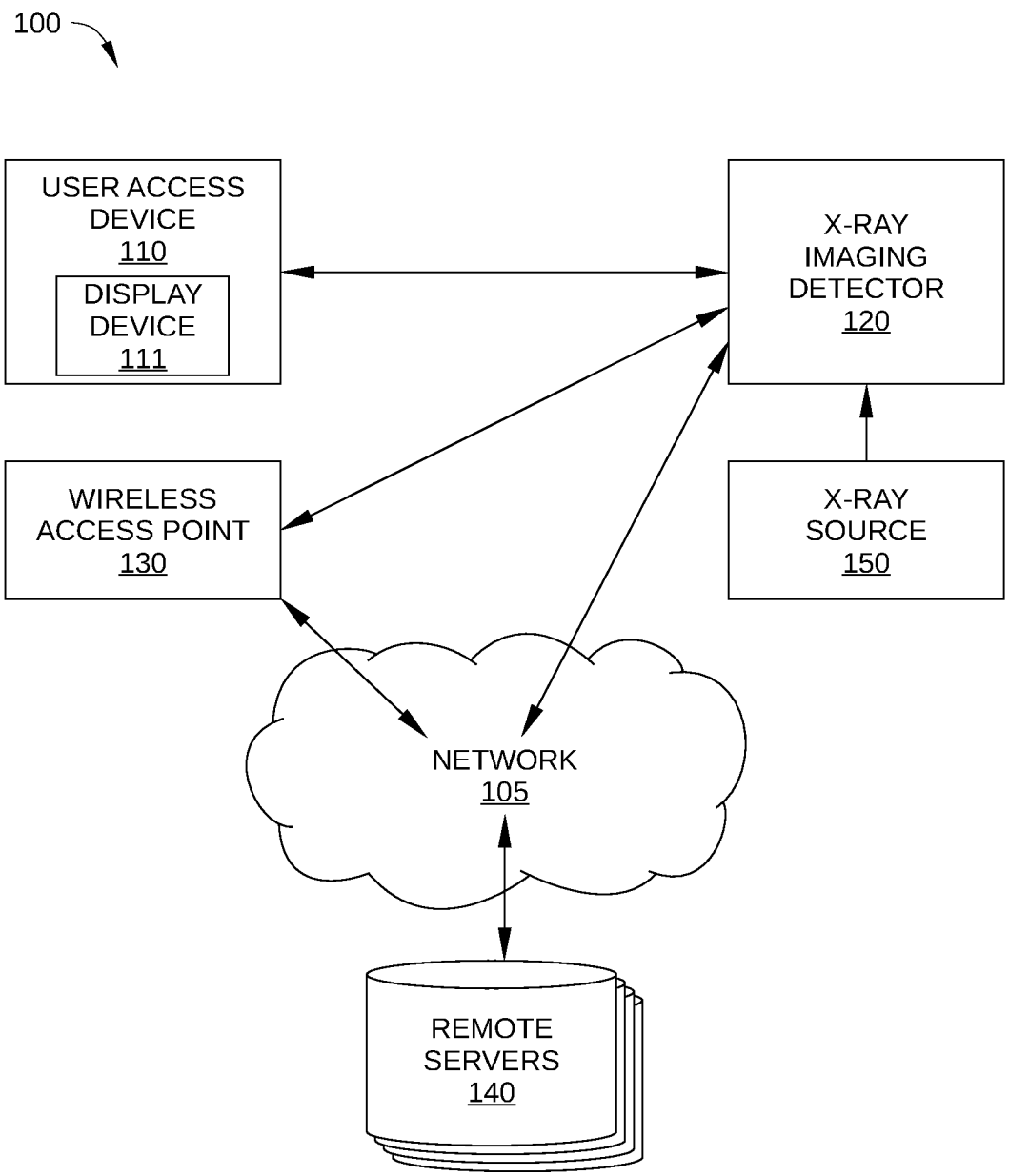
FIG. 1 is a block diagram of a digital radiographic X-ray acquisition system, according to one or more embodiments of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

In light of the description of the prior art above, there is a need in the art for a portable X-ray digital imaging apparatus that is battery powered and includes user interface, image acquisition, image enhancement, data storage and data transmission capabilities.

According to embodiments of the present disclosure, an imaging detector is configured to download study data from one or more external servers, generate a digital representation of an x-ray image, and associate the digital representation to the study data.

In addition, according to embodiments of the present disclosure, a digital X-ray image is generated via a portable, battery-powered, X-ray sensor system, and made available to a user via a user's computing device, such as a smartphone, laptop computer, or electronic tablet. The X-ray sensor system is configured to perform image processing and the user's computing device displays a user interface (UI) for interacting with the X-ray system. Consequently, the functionality of a conventional radiographic X-ray acquisition system is provided without an external data acquisition and processing workstation. Furthermore, the X-ray sensor system has a power state architecture that can significantly reduce power consumption, thereby enabling use of the X-ray system as a portable, battery-powered device. Specifically, the X-ray system is configured with a first power region that performs image acquisition and a second power region that performs UI, networking, and image processing functions. To save power, the processor associated with the first power region and the processor associated with the second power region can each independently enter a lower power consumption state, such as an idle state or a sleep state.

FIG. 1 is a block diagram of a digital radiographic X-ray acquisition system 100, according to one or more embodiments of the present disclosure. Digital radiographic X-ray acquisition system 100 is a digital radiography system that is configured to provide the functionality of a conventional radiographic X-ray acquisition system when paired with a user computing device. Thus, in addition to generating raw digital X-ray image data based on incident X-rays, digital radiographic X-ray acquisition system 100 is also configured to generate digital images based on the raw digital X-ray image data, perform suitable image processing of the digital images, and provide a UI that enables a user to access the digital images without a dedicated data acquisition workstation or other computing device. As shown, digital radiographic X-ray acquisition system 100 includes a user access device 110 wirelessly connected to an X-ray imaging detector 120, which in turn can connect to remote servers (external server) 140 via a network 105. In some embodiments, digital radiographic X-ray acquisition system 100 connects to remote servers 140 via a wireless access point 130.

Network 105 may be any technically feasible type of communications network that allows data to be exchanged between digital radiographic X-ray acquisition system 100 and remote servers 140. Examples of network 105 may include a wide area network (WAN), a local area network (LAN), a wireless (e.g., WiFi) network, and/or the Internet, among others.

Remote servers 140 are computing devices in which resides information pertinent to operation of X-ray imaging detector 120, such as user data, patient data, previously performed studies, and previously acquired images associated therewith. For example, in some embodiments, remote servers 140 include one or more Digital Image and Communications in Medicine (DICOM®) servers, such as a DICOM® picture archiving and communication system (PACS) storage server and/or a DICOM® PACS review workstation. Such servers provide storage and convenient access to medical images from multiple modalities, thereby enabling a user of X-ray imaging detector 120 to immediately access previously generated medical images and/or studies associated with a particular patient or project. In other examples, the servers provide storage and convenient access to other X-ray images used in industrial and security applications.

User access device 110 may be any technically feasible computing device that includes a display device 111 for displaying a UI and is capable of wirelessly connecting to X-ray imaging detector 120. For example, user access device 110 may be a smartphone and/or a wearable computing device, an electronic tablet, a laptop computer, and the like, that is configured to interact with (e.g., receive output from and provide input to) X-ray imaging detector 120. In some embodiments, user access device 110 is programmed with a software application that enables such interactions with X-ray imaging detector 120. A user access device 110 may enables such interactions, so X-ray imaging detector 120 does not require a dedicated data acquisition workstation, such as a desktop computer. As a result, X-ray imaging detector 120 can be configured in a more portable form factor. In addition, the power usage associated with a display device is externalized to user access device 110, further enhancing the portability of X-ray imaging detector 120 and duration of the operating time for X-ray imaging detector 120.

In some embodiments, user access device 110 interacts with X-ray imaging detector 120 via a web-browser-based interface. In such embodiments, X-ray imaging detector 120 is configured as a web server that transmits a UI to user access device 110 during operation of X-ray imaging detector 120. Furthermore, in such embodiments, to interact with X-ray imaging detector 120, user access device 110 may be any computing device that supports a suitable browser program, for example a Hypertext Markup Language-5-compliant (HTML5-compliant) Web browser program. Thus, X-ray imaging detector 120 can operate according to a "bring your own device" scheme, and therefore can be operated by a plurality of different users, each with a different user access device 110. As a result, the impact of repairing or completely replacing software executed by X-ray imaging detector 120 on the plurality of different users is greatly reduced, since each of the individual user access devices 110 is unaffected by such upgrades or repairs. In addition, such software upgrades are streamlined, since upgrades to each of the various user access devices 110 is not required.

X-ray imaging detector 120 is a battery powered, wireless radiographic panel that is configured with the functionality of an X-ray image acquisition workstation in the form factor of a portable X-ray imaging detector. As such, capabilities of X-ray imaging detector 120 include, without limitation, one or more of: image processing capability for radiographic (single image X-ray) applications; image processing capability for fluoroscopic (video X-ray) applications; querying over a wireless network, such as network 105, downloading or uploading study data from the remote server, such as a DICOM® Modality Worklist Server included in remote servers 140; locally storing study data to be performed, similar to a DICOM® Modality Worklist Server, which can be dynamically synchronized with one or more of remote servers 140; providing a user interface, via an internal Web server, to access a locally stored study data in a database or electronic storage device (e.g., flash memory); maintaining a local record of studies performed and images acquired, such as a panel-resident version of a DICOM® PACS; providing a user interface to view and/or review such studies; transmitting studies performed, including images, directly from X-ray imaging detector 120 to one or more of remote servers 140; the ability to be simultaneously connected to both user access device 110 and to network-resident resources residing in one or more of remote servers 140; and the ability to undergo software repair or replacement without the need for a separate computing device, such as a dedicated workstation computer. In addition, in some embodiments, capabilities of X-ray imaging detector 120 include, without limitation, enhancement of digital images using enhancement algorithms running on X-ray imaging detector 120 (rather than being performed in a dedicated acquisition workstation). Thus, in such embodiments, X-ray imaging detector 120 can provide the necessary enhancement algorithms. Standard image processing can include offset correction, gain correction, and defect correction. Offset correction shifts the baseline level of each pixel so that the pixels share the same baseline output level. Gain correction normalizes the response of each pixel to X-ray input. Together, offset and gain correction allow the collection of pixels that form the image to have a uniform response to X-ray input. In addition, imaging detectors can have at least a few pixels that are defective in some way, and can't be normalized using offset and gain correction. Defect correction replaces such defective pixels using an average of nearest neighbor pixels.

Three types of image enhancement algorithms (beyond standard image processing) that may be employed in various embodiments include: grid detection and suppression; scatter correction; and essential enhancement.

In grid detection and suppression, a one dimensional X-ray grid comprises a group of narrow, parallel strips of dense material, with a narrow gap between each strip. Such a grid can be used to reduce the obscuring effects of X-rays which are scattered by the subject's body or surrounding objects, without being absorbed. The grid detection and suppression algorithm can include various methods. The grid detection method determines if grid is present. The grid characterization and suppression methods are used if grid is present. Grid characterization determines attributes such as the frequency of the grid, the magnitude of the grid peak, the spread of the grid peak, and the orientation of the grid. Grid suppression includes a series of one-dimensional band-stop filters.

Scatter correction is an alternative (or supplemental) technique for reducing the effects of scattered, non-absorbed radiation. The effects of scatter of X-rays by the subject's body or other adjacent materials can be estimated by using a scatter kernel. This scatter kernel can be used to remove the contribution of scatter radiation from the overall signal, leaving only the desired signal due to primary (non-scattered) radiation.

In essential enhancement, an image is first processed for overall contrast and brightness enhancement based on the analysis of the data present in the image and exam based parameters. Then, the image is split in different frequencies that are enhanced adaptively based on analysis of input data as well as provided parameters. In so doing, the contrast, sharpness and noise level of organs, tissues and bone boundaries in the image is controlled. Essential enhancement algorithms make an image clinically useful when only basic image processing is applied to an X-ray image.

next step in processing is used to control the contrast, sharpness and noise level of organs, tissues and bone boundaries in the image. This is done via splitting the image in different frequencies and enhancing them adaptively based on analysis of input data as well as provided parameters.

A DICOM® Modality Worklist Server is a service defined by the DICOM® standard that provides a list of scheduled studies when queried by a modality, such as an X-ray acquisition system. A DICOM® Storage Server is a service that provides storage of performed studies.

Study data can include a list of patients, studies to be performed (also referred to as worklists), one or more studies that have already been performed, and image data. In one embodiment, a study is an entity (e.g., a container) that represents a single image capture event. In some embodiments, a study may be scheduled (not yet performed), in which case the study would have patient data associated therewith, but may not have associated images. Once the study has been performed (e.g., a patient shows up, images are captured, etc.), then images can be attached to the study.

In operation, an X-ray source 150 directs X-rays through a patient or object of interest and onto X-ray imaging detector 120. In embodiments in which X-ray imaging detector 120 is configured as an indirect panel detector, a scintillator material in X-ray imaging detector 120 is excited by the incident X-rays and emits light, which is detected by a plurality of photodiodes. Each diode generates a signal (e.g., a voltage that is proportional to incident light intensity) for a different pixel of what will eventually become an digital image, and an encoder in X-ray imaging detector 120 interprets each of these voltages and assigns a value to each that is proportional to the voltage. In embodiments in which X-ray imaging detector 120 is configured as a direct panel detector, incident X-ray photons are converted directly into charge.

Figure 2:
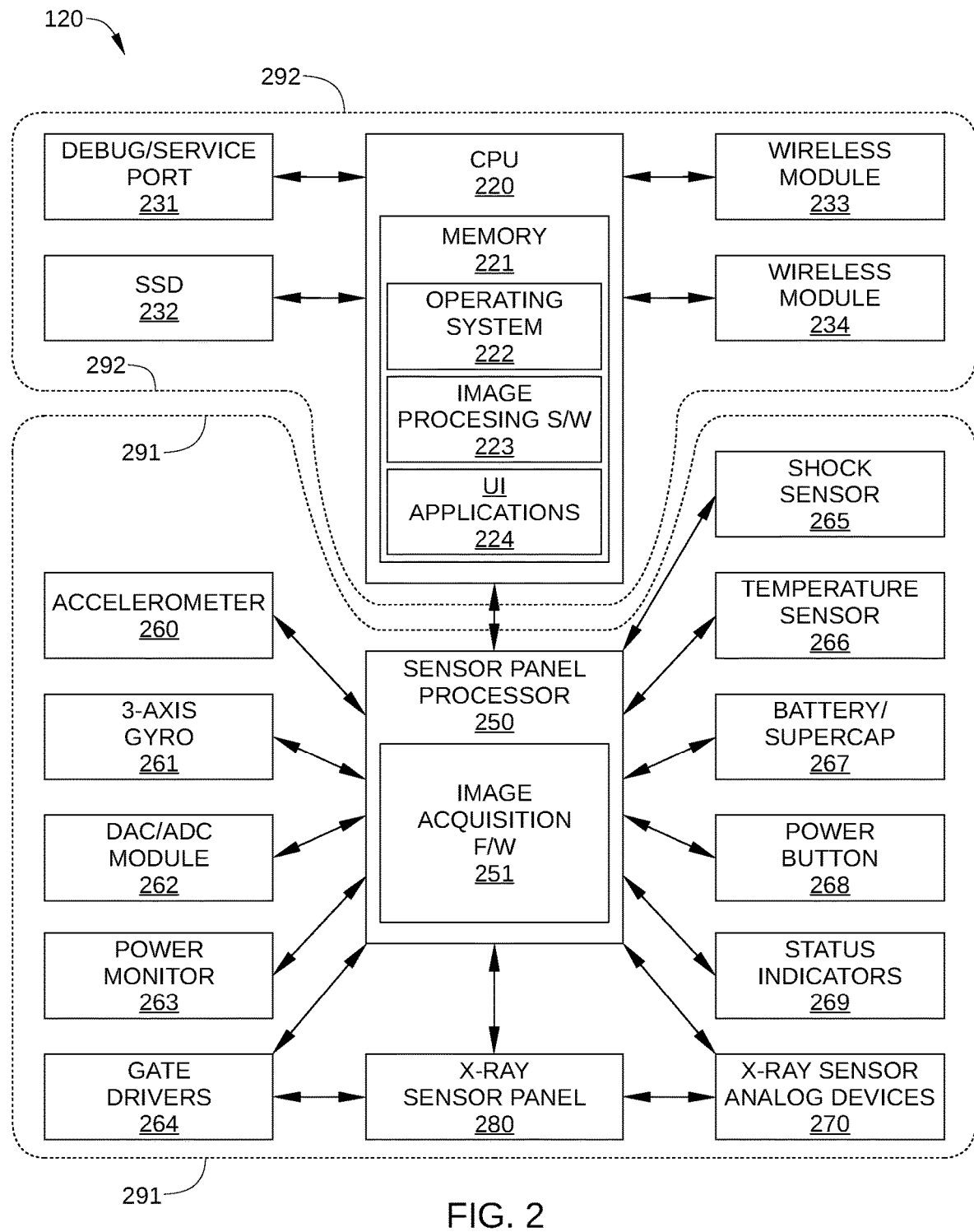
FIG. 2 schematically illustrates a portable X-ray imaging detector of the digital radiographic X-ray acquisition system in FIG. 1.

One embodiment of X-ray imaging detector 120 is described below in conjunction with FIG. 2. FIG. 2 schematically illustrates X-ray imaging detector 120, according to one or more embodiments of the present disclosure. As shown, X-ray imaging detector 120 includes a central processing unit (CPU) 220, a sensor panel processor 250, and an X-ray sensor panel 280. CPU 220 is coupled to various devices, including one or more of a debug/service port 231, a solid-state drive (SSD) 232 or other non-volatile data storage medium, and wireless transceiver (wireless modules 233 and 234). CPU 220 also includes or is coupled to a memory 221. Similarly, sensor panel processor 250 is coupled to various devices, including one or more of an accelerometer 260, a 3-axis gyro 261, a digital-to-analog converter/analog-to-digital converter (DAC/ADC) 261, a power monitor 263, gate drivers 264 for X-ray sensor panel 280, a shock sensor 265, a temperature sensor 266, a battery/supercapacitor 267 or other power source, a power button 268, status indicators 269, and X-ray sensor analog devices 270. In addition, sensor panel processor 250 includes or is coupled to image acquisition firmware 251.

CPU 220 may be any suitable processor implemented as a CPU, an application-specific integrated circuit (ASIC), a field programmable gate array (FPGA), any other type of processing unit, or a combination of different processing units. In some embodiments, CPU 220 is a Smart Mobility Architecture (SMARC) x86-based processor. In general, processing unit 220 may be any technically feasible hardware unit capable of processing data and/or executing software applications residing in memory 221, including an operating system (OS) 222, image processing software 223, and/or UI applications 224, among others, such as panel calibration software, study editing software, image review and/or annotation software, image reprocessing software, and the like. CPU 220 is configured to read data from and write data to memory 221. Memory 221 may include a random access memory (RAM) module, a flash memory unit, or any other type of memory unit or combination thereof. Memory 221 includes various software programs that can be executed by CPU 220 and application data associated with said software programs, including OS 222, image processing software 223, and/or UI applications 224, among others. For clarity, memory 221 is depicted as included in CPU 220 in FIG. 2, but in some embodiments can be implemented as a separate device.

OS 222 supports the functions of CPU 220, including scheduling tasks, executing image processing software 223 and UI applications 224, sending commands to SSD 232, wireless module 233, and wireless module 234, and managing the power state of CPU 220. Image processing software 223 includes one or more applications for processing image data received from sensor panel processor 250 to generate a digital image and/or to perform an enhancement algorithm on the digital image. For example, image processing software 223 may be configured to convert a digital representation or other image data into a digital image in a specific image file format and/or to modify the resultant digital image. Thus, once a digital representation is received from sensor panel processor 250, image generation and post-processing can be performed independently from the operation of X-ray sensor panel 280 and sensor panel processor 250. UI applications 224 include any software applications that enable wireless communication between X-ray imaging detector 120 and user access device 110 and between X-ray imaging detector 120 and remote servers 140. For example, UI applications 224 may be configured to generate and transmit a UI to user access device 110 (e.g., via a web browser) and to receive and implement user inputs received from user access device 110. Thus, UI applications 224 enable user access device 110 to be employed to control and otherwise interact with X-ray imaging detector 120. In such embodiments, CPU 220, UI applications 224, and wireless module 233 and/or 234 functions as a web server. Furthermore, in such embodiments, UI applications 224 can be configured for patient selection, image acquisition, image or study annotation, or review of images.

Debug/service port 231 provides a wired connection to X-ray imaging detector 120 for troubleshooting, software upgrades, and the like. SSD 232 provides non-volatile storage for previously acquired data or medical images, studies associated with a particular patient or project, and/or software applications. Wireless modules 233 and 234 may be any technically feasible wireless chips, cards, or other devices that enable X-ray imaging detector 120 to communicate wirelessly with user access device 110 in FIG. 1 and/or with wireless access point 130 in FIG. 1. Examples of devices suitable for use as wireless module 233 and/or 234 include a WiFi® module, a WLAN module, a 3G module, and the like. For example, in some embodiments, wireless module 233 and/or 234 is a 802.11ac/n device capable of providing a WiFi® Direct connection to user access device 110. Alternatively or additionally, in some embodiments, wireless module 233 and/or 234 is a device capable of providing a Bluetooth® connection to user access device 110. In some embodiments, at least one wireless transceiver is configured to communicate using a WiFi®, Institute of Electrical and Electronics Engineers (IEEE) 802.11 standard, Bluetooth®, or IEEE 802.15 wireless communication standard, a third generation partnership project (3GPP®) long term evolution (LTE®) (e.g., Release 11 or 12), High Speed Packet Access (HSPA), or IEEE 802.16 standard (e.g., 802.16e, 802.16m), which is commonly known to industry groups as WiMAX® (Worldwide interoperability for Microwave Access). Thus, in some embodiments, wireless modules 233 and/or 234 include two antennas and are capable of both WiFi® and Bluetooth® operation simultaneously. In some embodiments, wireless module 233 is configured for wireless communication with X-ray imaging detector 120 and wireless module 234 is configured for independent wireless communication with wireless access point 130, for example for communicating with the cloud or with remote servers 140. In such embodiments, wireless module 234 may be disabled to conserve power when X-ray imaging detector 120 is in a location without Internet access or a wireless access point 130.

Sensor panel processor 250 is a separate processor from CPU 220 that controls and otherwise interacts with the image acquisition hardware of X-ray imaging detector 120. As such, sensor panel processor 250 may be any suitable processor implemented as a CPU, an ASIC, an FPGA, any other type of processing unit, or a combination of different processing units. In some embodiments, sensor panel processor 250 is an FPGA that includes image acquisition firmware 251. In general, sensor panel processor 250 may be any technically feasible hardware unit capable of controlling the image acquisition hardware of X-ray imaging detector 120, receiving signals from the readout electronics of X-ray sensor panel 280, generating a digital representation of an x-ray image based on the received signals, and transmitting the digital representation to CPU 220 for image processing. In some embodiments, the sensor panel processor 250 may be functionality included in the CPU 220.

Accelerometer 260 and 3-axis gyro 261 indicate the precise orientation of X-ray imaging detector 120 during X-ray image acquisition, even when there is motion of X-ray imaging detector 120 at that time. Thus, metadata indicating up/down/left/right for a particular image can be collected at the time of image acquisition. In some embodiments, accelerometer 260 can also indicate when X-ray imaging detector 120 has been bumped, thereby preventing signals generated by X-ray sensor panel 280 during such a bump from being interpreted as an image signal generated in response to incident X-rays. In some embodiments, output from accelerometer 260 can be employed in a "shake-to-wake" feature, in which a user can cause X-ray imaging detector 120 to exit an idle or sleep state and enter a more active state simply by shaking X-ray imaging detector 120.

DAC/ADC 261 can facilitate generation of a digital representation of an image by converting each analog signal (voltage) received from each of the plurality of diodes disposed in X-ray sensor panel 280 to a digital value. Power monitor 263 monitors battery state. Gate drivers 264 amplify the output of each of the light-detecting diodes of X-ray sensor panel 280. Shock sensor 265 may include dedicated logic for detecting bumping or jarring of X-ray imaging detector 120 based on signals from accelerometer 260. Alternatively, shock sensor includes dedicated sensors for detecting bumping or jarring of X-ray imaging detector 120. Temperature sensor 266 monitors temperature of X-ray sensor panel 280 to facilitate temperature-based correction of the analog signals generated thereby. Battery/supercapacitor 267 serves as a power source for X-ray imaging detector 120. In some embodiments, batter/supercapacitor 267 is also configured as a temporary uninterrupted power supply or other power source for X-ray imaging detector 120 to facilitate battery hot-swapping. Status indicators 269 include visual indicators, such as one or more color-coded light-emitting diodes (LEDs) and/or audible indicators, such as one or more buzzers. Status indicators 269 can provide information to a user associated with one or more of current power state, battery state, wireless communication state, system state, completion of a current image acquisition, and the like. X-ray sensor analog devices 270 include the readout electronics of X-ray sensor panel 280, such as analog ASIC devices, that each generate a voltage that is proportional to incident visible light on a particular pixel of X-ray sensor panel 280.

Power button 268 enables various user inputs to control the power state of CPU 220, sensor panel processor 250, and/or X-ray imaging detector 120 as a whole. For example, in some embodiments, when X-ray imaging detector 120 is off, pressing power button 268 for more than a certain time interval, such as one second, results in sensor panel processor 250 turning on and booting up. In some embodiments, when X-ray imaging detector 120 is operating, pressing power button 268 for a longer time interval, for example between one and three seconds, results in CPU 220, sensor panel processor 250, and/or X-ray imaging detector 120 as a whole to exit any lower power state, such as an idle or sleep state, and enter a normal operating power state. In some embodiments, when X-ray imaging detector 120 is operating, pressing power button 268 for a still longer time interval, for example between three and six seconds, results in CPU 220 and sensor panel processor 250 attempting to shut down. In some embodiments, when X-ray imaging detector 120 is operating, pressing power button 268 for an even longer time interval, for example greater than six seconds, results in CPU 220 and sensor panel processor 250 immediately shutting down. In other embodiments, any other technically feasible user input scheme may be employed in conjunction with power button 268 to cause sensor panel processor 250 and/or CPU 220 to enter a certain power state.

According to various embodiments of the present disclosure, X-ray imaging detector 120 is configured with a power state architecture that includes a first power region 291 that performs image acquisition and a second power region 292 that performs UI and image processing functions. As shown, sensor panel processor 250 and X-ray sensor panel 280 are included in first power region 291 and CPU 220 and associated devices are included second power region 292. To save power, the processor associated with the first power region, i.e., sensor panel processor 250, and the processor associated with the second power region, i.e., CPU 220, can each independently enter an idle or other lower-power consumption state, such as a sleep state. Thus, sensor panel processor 250 and first power region 291 operate according to one power state scheme, described below in conjunction with FIG. 3, while CPU 220 and second power region 292 operate according to another power state scheme, described below in conjunction with FIG. 4.

Figure 3:
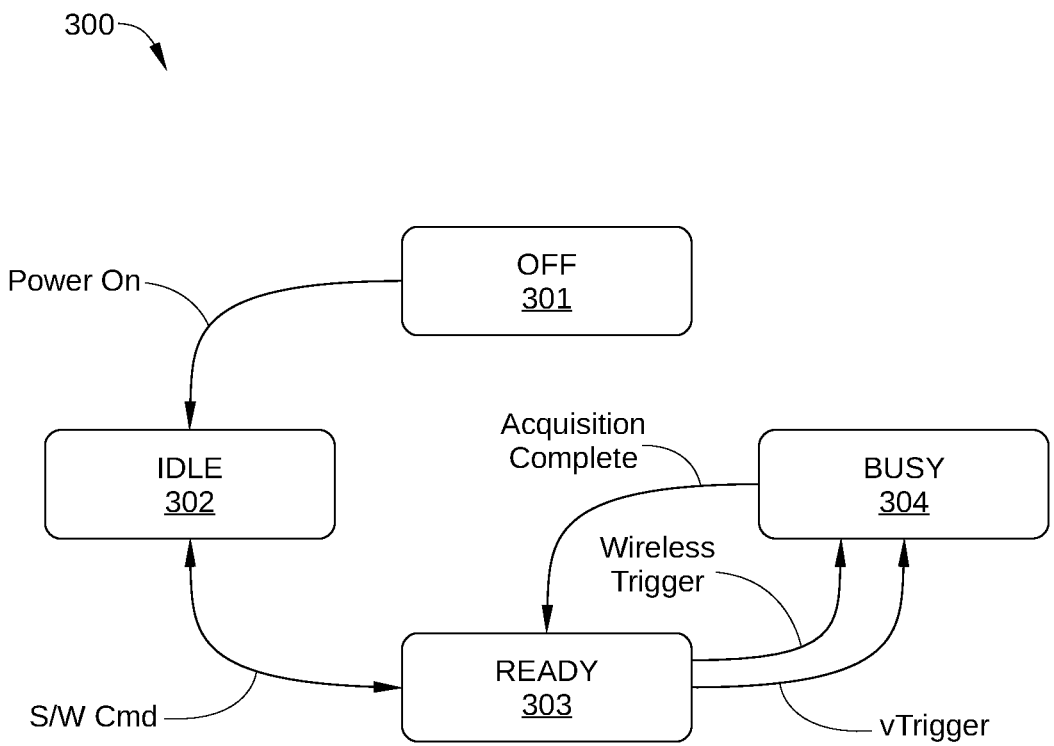
FIG. 3 is a power state diagram for a sensor panel processor and a first power region of the portable X-ray imaging detector of FIG. 2, according to various embodiments of the present disclosure.

FIG. 3 is a power state diagram 300 for sensor panel processor 250 and first power region 291, according to various embodiments of the present disclosure. As shown, sensor panel processor 250 operates in four different power states: an off state 301, an idle state 302, a ready state 303, and a busy state 304.

In idle state 302, X-ray sensor analog devices 270, i.e., the light sensors of X-ray sensor panel 280, are powered, but in a resting state, i.e., low voltages are applied to X-ray sensor analog devices 270. In addition, in some embodiments, in idle state 302 X-ray sensor analog devices 270 do not respond to positive gate voltages (typically generated by incident X-rays) greater than a predetermined threshold value, for example one volt. Little power is required for idle state 302 and, as a result, X-ray sensor panel can remain in idle state 302 with relatively low power consumption.

In ready state 303, X-ray sensor analog devices 270 are powered and ready to detect X-ray exposure. Thus, incident X-rays can generate voltages higher than the predetermined threshold value of idle state 302. Because X-ray sensor analog devices 270 are in a low power state, but can detect incident X-rays, ready state 303 can be considered a "vTrigger" state. In this power state, once incident X-rays are detected, image acquisition can be triggered by causing X-ray sensor panel 280 to enter busy state 304. In an embodiment, the trigger can be from a user access device ("Wireless Device") or a "vTrigger."

In busy state 304, X-ray sensor panel 280 performs image acquisition, i.e., waiting for an integration time, reading out X-ray sensor analog devices 270, and in some embodiments, waiting for another integration time for a post-offset image and reading out X-ray sensor analog devices 270 a second time.

As shown, sensor panel processor 250 and X-ray sensor panel 280 enter idle state 302 from off state 301 in response to a power on indicator, for example, when a user depresses power button 268 for more than one second. Sensor panel processor 250 and X-ray sensor panel 280 enter idle state 302 from ready state 303 in response to a software command. Such a software command may be generated in response to a user input from user access device 110 (shown in FIG. 1), to X-ray sensor panel 280 remaining idle for more than a maximum threshold time, etc. Similarly, sensor panel processor 250 and X-ray sensor panel 280 enter ready state 303 from idle state 302 in response to such a software command. In addition, sensor panel processor 250 and X-ray sensor panel 280 enter ready state 303 from busy state 304 in response to completion of the acquisition of an image. Sensor panel processor 250 and X-ray sensor panel 280 enter busy state 304 from ready state 303 in response to a vTrigger, i.e. when X-ray sensor analog devices 270 detect incident X-rays when X-ray sensor panel 280 is in ready state 303. Alternatively or additionally, sensor panel processor 250 and X-ray sensor panel 280 enter busy state 304 from ready state 303 in response to a wireless trigger, such as a transmission from user access device 110.

Figure 4:
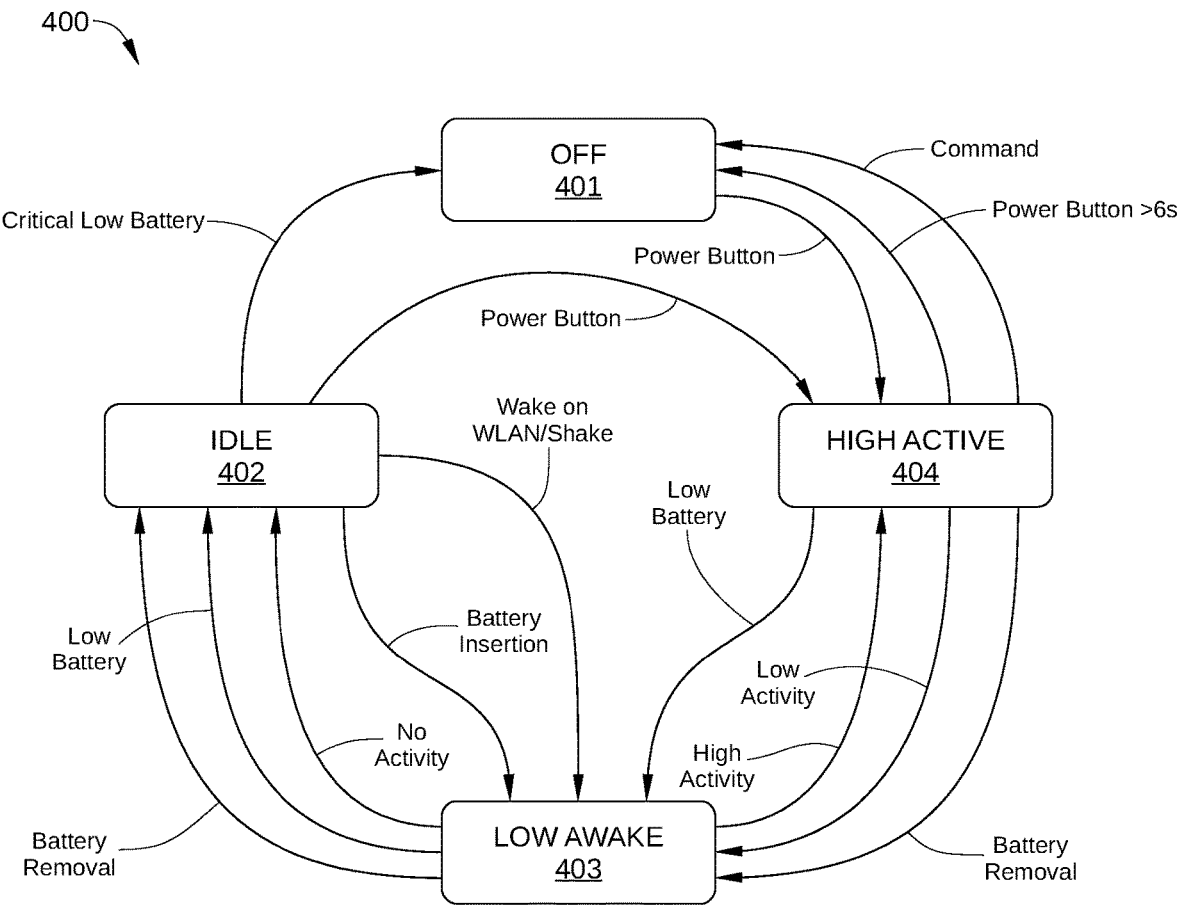
FIG. 4 is a power state diagram for a CPU and a second power region of the portable X-ray imaging detector of FIG. 2, according to various embodiments of the present disclosure.

In some embodiments, when sensor panel processor 250 and X-ray sensor panel 280 enter idle state 302 from off state 301, sensor panel processor 250 powers up CPU 220 (see FIG. 4). Thus, in such embodiments, sensor panel processor 250 controls the initial power state of CPU 220. In addition, in some embodiments, when sensor panel processor 250 and X-ray sensor panel 280 are in ready state 303 and X-rays are detected, sensor panel processor 250 causes CPU 220 to exit a sleep or idle state if CPU 220 is in such a state. For example, sensor panel processor 250 can transmit a "wake on WLAN" command (see FIG. 4). In such embodiments, CPU 220 and second power region 292 are thereby made ready to process and display images for a user with reduced or minimal delay, but can remain in a lower power consumption state when no images are being acquired by sensor panel processor 250 and X-ray sensor panel 280.

FIG. 4 is a power state diagram 400 for CPU 220 and second power region 292, according to various embodiments of the present disclosure. As shown, CPU 220 operates in four different power states: an off state 401, a sleep state 402, a low awake state 403, and a high active state 404.

In idle state 402, no software is operating in CPU 220. In some embodiments, idle state 402 is substantially similar to an S3 sleep state. In such embodiments, CPU 220 operates according to a typical S3 power state, including entering off state 401 when a critical battery power is detected, and entering high active state 404 when power button 268 is depressed for a particular duration of time (e.g., one to three seconds). Similarly, CPU 220 enters idle state 402 from low awake state 403 in response to a battery removal event, low battery detection, or no activity for more than a maximum time threshold. In addition, in some embodiments, in idle state 402 CPU 220 is configured to enter low awake state 403 when a battery insertion is detected, or when CPU 220 receives a "wake on WLAN," for example in response to detection of X-rays, and/or when CPU 220 receives a shake input from sensor panel processor 250. In some embodiments, a PCI Express (PCIe) wake mechanism is employed to cause CPU 220 to enter low awake state 403 from idle state 402. In some embodiments, wireless module 233 or 234 is programmed to assert a PCIe Wake signal when a particular type of packet is detected from sensor panel processor 250. It is noted that CPU 220 can be in idle state 402 while sensor panel processor 250 is in ready state 303 or busy state 304, thereby avoiding unnecessary energy consumption by X-ray imaging detector 120.

In low awake state 403, CPU 220 operates in a lower power consumption state (i.e., a lower activity level operating state), such as an S0 low awake state. Low awake state 403 is a lower power consumption state than a normal operating state, such as high active state 404. Thus, one or more cores of CPU 220 are parked if not executing software. CPU 220 enters low awake state 403 from high active state 404 in response to low battery detection, low activity detection, or a battery removal event.

In high active state 404, CPU 220 operates a standard operating state, such as an S0 high active state. Thus, CPU 220 enters high active state 404 from off state 401 in response to power button 268 being depressed, from sleep state 402 in response to power button 268 being depressed, and from low awake state 403 in response to detecting a high activity level. In addition, CPU 220 enters off state 401 from high active state 404 in response to power button 268 being depressed for an extended duration, such as greater than six seconds, or in response to a software command, for example via a user input to user access device 110.

As illustrated by power state diagram 400, CPU 220 and second power region 292 are configured to enter a lower power consumption state independently from sensor panel processor 250 (or functionality) and first power region 291. For example, during a period of time in which a large number of images are acquired but no image processing or communication with remote servers 140 is required, CPU 220 and second power region 292 can remain in low awake state 403 or sleep state 402 while sensor panel processor 250 and X-ray sensor panel 280 operate in ready state 303 and/or busy state 304, thereby greatly reducing power consumption of X-ray imaging detector 120. Thus, by operating CPU 220 and second power region 292 in a lower power consumption state until image processing is needed for an acquired image, a significant reduction in power consumption of X-ray imaging detector 120 can be realized. It is noted that for a typical processor, power consumption in high active state 404 may be on the order of about 20 W, power consumption in low awake state 403 may be on the order of about 5 W, and power consumption in sleep state 402 may be on the order of about 0.5 W.

Figure 5:
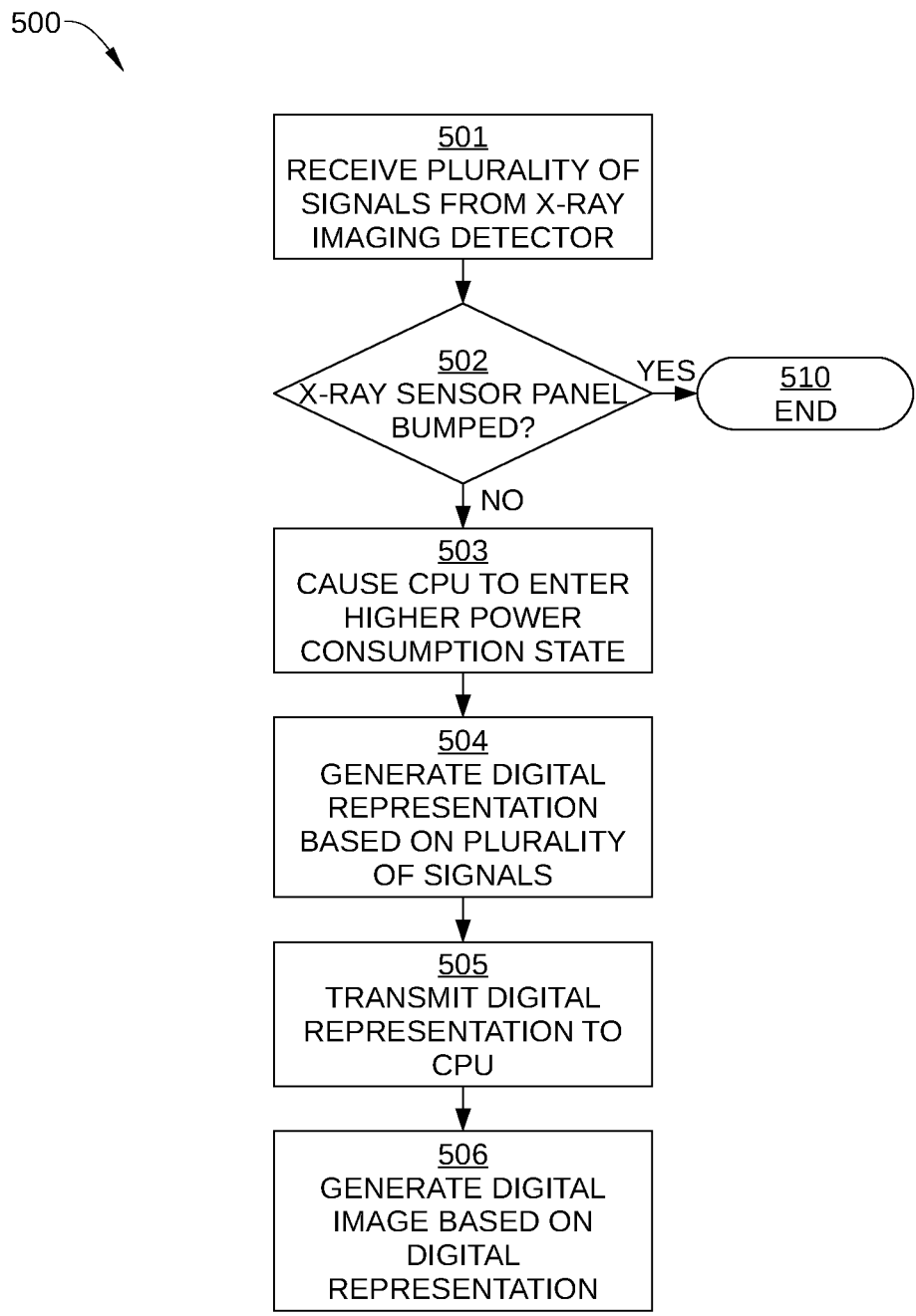
FIG. 5 sets forth a flowchart summarizing an example method for acquiring an X-ray image, according to one or more embodiments of the present disclosure.

FIG. 5 sets forth a flowchart summarizing an example method for acquiring an X-ray image, according to one or more embodiments of the present disclosure. The method may include one or more operations, functions, or actions as illustrated by one or more of blocks 501-510. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with digital radiographic X-ray acquisition system 100 of FIGS. 1-4, persons skilled in the art will understand that any suitably configured radiographic system is within the scope of the present disclosure.

Prior to the method step, sensor panel processor 250 and first power region 291 enter ready state 303, for example in response to a user starting up X-ray imaging detector 120 via power button 268. In addition, CPU 220 and second power region 292 enter sleep state 402, for example in response to the detection of low activity in CPU 220.

A method 500 begins at step 501, in which sensor panel processor 250 detects X-rays incident on X-ray sensor panel 280 via a plurality of signals from X-ray sensor panel 280. For example, in some embodiments, X-ray sensor analog devices 270 each transmit a voltage signal to sensor panel processor 250 in response to incident light generated by a scintillator material disposed on X-ray sensor panel 280, where the scintillator material emits visible light when excited by incident X-rays.

In step 502, sensor panel processor 250 determines whether the plurality of signals are associated with a bumping or jarring of X-ray sensor panel 280, based on outputs from accelerometer 260 and/or shock sensor 265. If yes, method 500 proceeds to step 510 and ends; if no, method 500 proceeds to step 503.

In step 503, sensor panel processor 250 (or sensor panel processor functionality) causes CPU 220 (or CPU functionality) to enter a higher power consumption state, such as high active state 404 or low awake state 403. For example, in some embodiments, sensor panel processor 250 transmits a wake on WLAN packet to CPU 220 via wireless module 233 or 234.

In step 504, sensor panel processor 250 generates a digital representation of an X-ray image based on the plurality of signals received in step 501. For example, the digital representation may include an intensity value for each pixel of X-ray sensor panel 280, as well as suitable metadata associated with the intensity values.

In step 505, sensor panel processor 250 transmits the digital representation of the X-ray image to CPU 220 for subsequent image processing. It is noted that CPU 220 is in an active state, such as high active state 404 or low awake state 403 during step 505, and therefore is ready to immediately begin the process of generating an image from the digital representation transmitted.

In step 506, CPU 220 generates a digital image based on the digital representation transmitted in step 505, such as a digital image file in a standard image format (e.g., bmp, gif, jpg, tif, etc.).

In X-ray radiography, alternating current (AC) noise can affect the quality of digital images generated by X-ray imaging detector 120 when an AC noise source is proximate X-ray sensor panel 280. For example, switching of the millions of transistors in CPU 220 in the GHz regime can be one such noise source. According to some embodiments, the switching of some or all components in X-ray imaging detector 120 is synchronized during operation. As a result, the impact of switching noise in images generated by X-ray imaging detector 120 can be made static from image to image. Consequently, the subtraction of an offset image from an acquired image will also remove such static noise. It is noted that the technique of subtracting an offset image (i.e., an image taken immediately after an exposed image but containing no dose) from an acquired image is generally used to compensate for temperature-induced and other short-term drift of the ASICs in X-ray sensor panel 280 used to read charge.

According to some embodiments, all the switching in X-ray imaging detector 120 is synchronized. Because various devices in X-ray imaging detector 120 that act as noise sources may asynchronously enter or exit a sleep mode during normal operation, in some embodiments a synchronization clock is modified to compensate for such asynchronous sleeping and waking of devices. According to such embodiments, CPU 220 and other noise source devices are synchronized to a single clock. Because processors suitable for use as CPU 220 typically are not designed to be synchronized to a single external clock, X-ray imaging detector 120 is synchronized to CPU 220 and not vice-versa.

Figure 6:
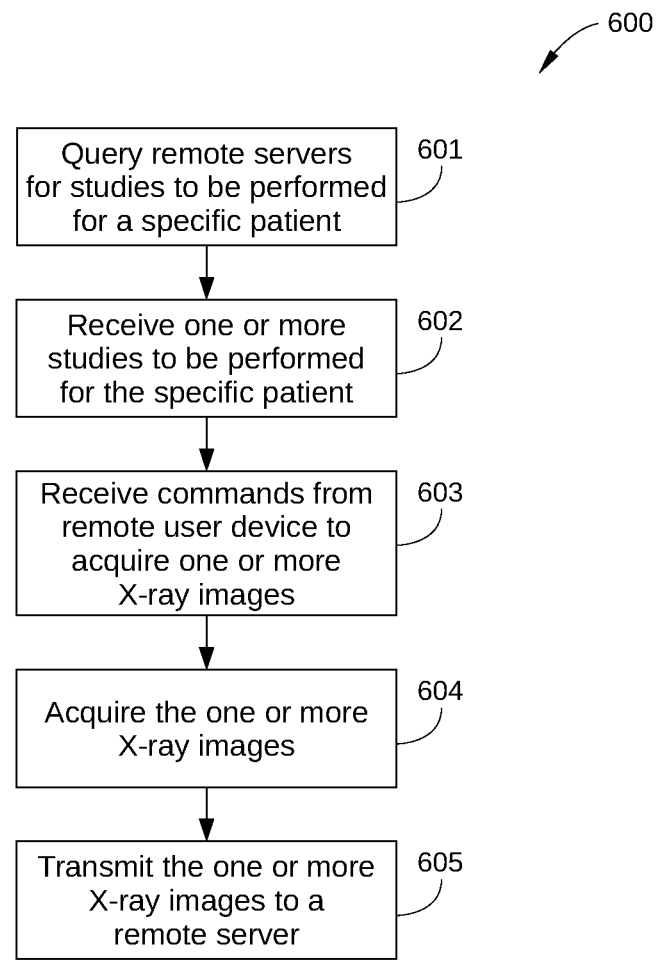
FIG. 6 sets forth a flowchart summarizing an example method for acquiring an X-ray image, according to one or more embodiments of the present disclosure.

FIG. 6 sets forth a flowchart summarizing an example method for acquiring an X-ray image, according to one or more embodiments of the present disclosure. The method may include one or more operations, functions, or actions as illustrated by one or more of blocks 601-605. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with digital radiographic X-ray acquisition system 100 of FIGS. 1-5, persons skilled in the art will understand that any suitably configured radiographic system is within the scope of the present disclosure.

Prior to the method step, a patient study is scheduled for a particular clinical location and stored in remote servers 140.

A method 600 begins at step 601, in which X-ray imaging detector 120 queries one or more remote servers 140 for one or more studies to be performed for a particular patient. In some embodiments, a user initiates the query via user access device 110 and X-ray imaging detector 120 the communicates with one or more remote servers 140 via wireless access point 130 or network 105. For example, X-ray imaging detector 120 may query a DICOM® Modality Worklist Server.

In step 602, X-ray imaging detector 120 receives one or more studies to be performed on the particular patient from remote servers 140, such as a DICOM® Modality Worklist Server.

In step 603, X-ray imaging detector 120 receives commands from user access device 110 to acquire one or more X-ray images.

In step 604, X-ray imaging detector 120 acquires and locally stores the one or more X-ray images. For example, in some embodiments, the acquired X-ray images and/or digital representations of the acquired X-ray images are stored in SSD 232. Consequently, a user can subsequently access such X-ray images or digital representations thereof via user access device 110 and without accessing a remote server 140.

In step 605, X-ray imaging detector 120 transmits the one or more X-ray images to one of remote servers 140. It is noted that such direct upload of image data provides for real-time availability of studies for review on a hospital PACS, without having to connect X-ray imaging detector 120 to a dedicated workstation. Similarly, direct download of worklist data provides for real-time updates to worklists (i.e., studies to be acquired), without having to connect X-ray imaging detector 120 to a dedicated workstation. It is further noted that in a conventional digital radiographic X-ray acquisition system, the above steps are generally coordinated and performed by software running on a separate computer workstation. According to various embodiments, using X-ray imaging detector 120, such software actually runs on X-ray imaging detector 120 itself. Thus, the user accesses the panel software via a "dumb" device (e.g., user access device 110). That is, the device can provide user access to panel software with the inclusion of an HTML5-compliant browser, and little or no other installed proprietary software.

The functionality of a conventional radiographic X-ray acquisition system can be provided without an external data acquisition and processing workstation. Thus, a digital X-ray image is generated via a portable, battery-powered, X-ray sensor system, and made available to a user via the user's computing device. The X-ray system is configured with a first power region that performs image acquisition and a second power region that performs user interface, networking, and image processing functions. To save power, the processor associated with the first power region and the processor associated with the second power region can each independently enter a lower power consumption state, such as an idle state or a sleep state.

Referring to FIGS. 1, 2, and 6, some embodiments include an X-ray imaging detector 120 comprises: at least one wireless module 233 or 234 configured to download study data from at least one remote server 140; an X-ray sensor panel 280 configured to generate a plurality of signals in response to X-rays incident on the X-ray imaging detector 120; and at least one sensor panel processor 250 or CPU 220 communicatively coupled to the X-ray sensor panel 280 and the at least one wireless module 233 or 234 and configured to: receive the plurality of signals and generate a digital representation of an x-ray image based on the plurality of signals, and associate the digital representation to the study data.

In some embodiments, the study data includes study and patient information and the remote server 140 includes a Digital Image and Communications in Medicine (DICOM®) modality worklist server.

In some embodiments, the at least one wireless module 233 or 234 is further configured to communicate using WiFi®, Institute of Electrical and Electronics Engineers (IEEE) 802.11 standard, Bluetooth®, IEEE 802.15 wireless communication standard, third generation partnership project (3GPP) long term evolution (LTE) (e.g., Release 11 or 12), High Speed Packet Access (HSPA), WiMax®, or IEEE 802.16 standard.

In some embodiments, the X-ray imaging detector 120 further comprises at least one SSD 232 communicatively coupled to the at least one sensor panel processor 250 or CPU 220 and a database configured to store the study data and the digital representation.

In some embodiments, the at least one wireless module 233 or 234 is further configured to upload study data to the at least one remote server 140, including a Digital Image and Communications in Medicine (DICOM®) Picture Archiving and Communication System (PACS) storage server.

In some embodiments, the at least one sensor panel processor 250 or CPU 220 is further configured to synchronize the study data stored on the X-ray imaging detector 120 with the at least one external server.

In some embodiments, the at least one sensor panel processor 250 or CPU 220 is further configured to generate a user interface and to cause a digital image based on the digital representation of the x-ray image or the study data to be displayed via the user interface.

In some embodiments, the X-ray imaging detector 120 further comprises a display communicatively coupled to the at least one processor and configured to view the user interface.

In some embodiments, the at least one wireless module 233 or 234 is communicatively coupled to a user access device 110.

In some embodiments, the X-ray imaging detector 120 further comprises at least one web server communicatively coupled to the at least one sensor panel processor 250 or CPU 220 and configured to communicate with the user access device 100.

In some embodiments, the user interface uses a Hypertext Markup Language-5-compliant (HTML5-compliant) web interface.

In some embodiments, the user interface is configured for patient selection, image acquisition, image or study annotation, or review of images.

In some embodiments, the at least one sensor panel processor 250 or CPU 220 is further configured to perform an enhancement algorithm on the digital image.

In some embodiments, the at least one sensor panel processor 250 or CPU 220 includes: the sensor panel processor 250 communicatively coupled to the X-ray sensor panel 280 and configured to receive the plurality of signals and generate the digital representation of the x-ray image based on the plurality of signals; and the CPU 220 configured to generate a user interface and to cause a digital image based on the digital representation of the x-ray image to be displayed via the user interface. In such embodiments, the sensor panel processor 250 is configured to enter a first idle state while the CPU 220 is in a second active state or the CPU 220 is configured to enter a second idle state while the sensor panel processor 250 is in a first active state.

In some embodiments, the CPU 220 is configured to receive the digital representation of the x-ray image and generate the digital image based on the digital representation of the x-ray image.

In some embodiments, the sensor panel processor 250 is configured to enter the first idle state after a time interval in which no x-rays are detected exceeds a threshold value.

In some embodiments, the first active state comprises a power state in which the X-ray imaging detector 120 generates the plurality of signals in response to x-rays incident on the X-ray imaging detector 120.

In some embodiments, the CPU 220 is configured to enter the second active state from the second idle state in response to a wake command from the sensor panel processor 250.

In some embodiments, the sensor panel processor 250 generates the wake command in response to one of a user input or detection of x-rays by the X-ray imaging detector 120.

In some embodiments, the CPU 220 is configured to execute an operating system that enables generation of the user interface.

According to some embodiments, an X-ray imaging device comprises a wireless communication means (e.g., wireless modules 233 and 234) configured to download study data from at least one external server (e.g., remote servers 140); a digital image sensing means (e.g., X-ray sensor panel 280) configured to generate a plurality of signals in response to x-rays incident on the digital image sensing means; and a controlling means (e.g., sensor panel processor 250 and CPU 220) configured to: receive the plurality of signals and generate a digital representation of an x-ray image based on the plurality of signals, and associate the digital representation to the study data.

Examples of a wireless communication means configured to download study data from at least one remote server 140 include wireless modules 233 and/or 234.

Examples of a digital image sensing means configured to generate a plurality of signals in response to x-rays incident on the digital image sensing means include X-ray sensor panel 280.

Examples of a controlling means configured to receive the plurality of signals and generate a digital representation of an x-ray image based on the plurality of signals and associate the digital representation to the study data include sensor panel processor 250 and/or CPU 220.

According to some embodiments, an apparatus comprises an X-ray imaging detector 120 configured to generate a plurality of signals in response to x-rays incident on the X-ray imaging detector 120 during an exposure period; a sensor panel processor 250 communicatively coupled to the X-ray imaging detector 120 and configured to receive the plurality of signals and generate a digital representation of an x-ray image based on the plurality of signals; and a CPU 220 configured to generate a user interface and to cause a digital image based on the digital representation of the x-ray image to be displayed via the user interface, wherein the sensor panel processor 250 is configured to enter a first idle state while the CPU 220 is in a second active state or the CPU 220 is configured to enter a second idle state while the sensor panel processor 250 is in a first active state.

According to some embodiments, a method for X-ray imaging detector 120 to process study data, comprises: downloading, by at least one wireless modules 233 or 234, the study data from at least one remote servers 140; generating a plurality of signals, by X-ray sensor panel 280, in response to x-rays incident on X-ray sensor panel 280; generating a digital representation of an x-ray image, by sensor panel processor 250, based on the plurality of signals; and associating the digital representation, by CPU 220 sensor panel processor 250, to the study data.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the claims beginning with claim [x] and ending with the claim that immediately precedes this one," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. An imaging detector, comprising:
    a digital image sensor configured to generate a plurality of signals in response to x-rays incident on the sensor;
    a first processor communicatively coupled to the digital image sensor and configured to receive the plurality of signals and generate a digital representation of an x-ray image based on the plurality of signals; and
    a second processor configured to generate a user interface and to cause a digital image based on the digital representation of the x-ray image to be displayed via the user interface, and
    wherein the first processor is configured to enter a first idle state while the second processor is in a second active state or the second processor is configured to enter a second idle state while the first processor is in a first active state.

2. The imaging detector of claim 1, further comprising:
    at least one wireless transceiver configured to download study data from at least one external server,
    wherein at least one of the first processor or the second processor is communicatively coupled to the sensor, and the at least one wireless transceiver is configured to associate the digital representation to the study data.

3. The imaging detector of claim 2, wherein the study data includes study and patient information and the external server includes a modality worklist server using an International Organization for Standardization (ISO) standard.

4. The imaging detector of claim 2, wherein the at least one wireless transceiver is further configured to communicate using Institute of Electrical and Electronics Engineers (IEEE) 802.11 standard, IEEE 802.15 wireless communication standard, third generation partnership project long term evolution standard release 11, third generation partnership project long term evolution standard release 12, or IEEE 802.16 standard.

5. The imaging detector of claim 2, further comprising at least one electronic storage device communicatively coupled to the at least one of the first processor or the second processor and a database configured to store the study data and the digital representation.

6. The imaging detector of claim 5, wherein the at least one wireless transceiver is further configured to upload study data to at least one of an external server and a modality worklist server using an ISO standard.

7. The imaging detector of claim 6, wherein the at least one of the first processor or the second processor is further configured to synchronize the study data stored on the imaging detector with the at least one external server.

8. The imaging detector of claim 2, wherein the second processor is further configured to cause the digital image based on the digital representation of the x-ray image or the study data to be displayed via the user interface.

9. The imaging detector of claim 8, further comprising a display communicatively coupled to the second processor and configured to view the user interface.

10. The imaging detector of claim 8, wherein the at east one wireless transceiver is communicatively coupled to a user access device.

11. The imaging detector of claim 10, further comprising at least one web server communicatively coupled to the at least one of the first processor or the second processor and configured to communicate with the user access device.

12. The imaging detector of claim 8, wherein the user interface uses a Hypertext Markup Language-5-compliant (HTML5-compliant) web interface.

13. The imaging detector of claim 8, wherein the user interface is configured for patient selection, image acquisition, image or study annotation, or review of images.

14. The imaging detector of claim 2, wherein the at least one of the first processor or the second processor is further configured to perform an enhancement algorithm on the digital image.

15. The imaging detector of claim 1, wherein the second processor is configured to receive the digital representation of the x-ray image and generate the digital image based on the digital representation of the x-ray image.

16. The imaging detector of claim 1, wherein the first processor is configured to enter the first idle state after a time interval in which no x-rays are detected exceeds a threshold value.

17. The imaging detector of claim 1, wherein the fist active state comprises a power state in which the imaging detector generates the plurality of signals in response to x-rays incident on the imaging detector.

18. The imaging detector of claim 1, wherein the second processor is configured to enter the second active state from the second idle state in response to a wake command from the first processor.

19. The imaging detector of claim 18, wherein the first processor generates the wake command in response to one of a user input or detection of x-rays by the imaging detector.

20. The imaging detector of claim 1, wherein the second processor is configured to execute an operating system that enables generation of the user interface.

21. An X-ray imaging device, comprising:
a digital image sensing means configured to generate a plurality of signals in response to x-rays incident on the sensor;
a first processing means communicatively coupled to the digital image sensing means and configured to receive the plurality of signals and generate a digital representation of an x-ray image based on the plurality of signals; and
a second processing means configured to generate a user interface means and to cause a digital image based on the digital representation of the x-ray image to be displayed via the user interface, and
wherein the first processing means is configured to enter a first idle state while the second processing means is in a second active state or the second processing means is configured to enter a second idle state while the first processing means is in a first active state.

22. The X-ray imaging device of claim 21, further comprising:
a wireless communication means configured to download study data from at least one external server,
wherein the first processing means or the second processing means is configured to associate the digital representation to the study data.

23. A method of generating a digital image with an image detector, comprising:
generating a plurality of signals, by a digital image sensor of the image detector, in response to x--rays incident on the sensor;
generating a digital representation of an x-ray image, by a first processor of the image detector that is in a first active state, based on the plurality of signals;
causing, in response to generating a plurality of signals, a second processor that is in a second idle state to enter a second active state by transmitting a wake signal to the second processor from the first processor; and
transmitting the digital representation to the second processor while the second processor is in the second active state.

24. The method of claim 22, further comprising:
executing, while the second processor is in the second active state, an operating system that enables generation of a user interface.

25. The method of claim 23, further comprising:
downloading, by at least one wireless transceiver of the image detector, the study data from at least one external server; and
associating the digital representation, by the first processor or the second processor of the image detector, to the study data.

* * * * *